United States Patent [19]
Weder

[11] Patent Number: 6,059,819
[45] Date of Patent: May 9, 2000

[54] THERAPEUTIC DEVICE

[75] Inventor: Donald E. Weder, Highland, Ill.

[73] Assignee: Southpac Trust International, Inc.

[21] Appl. No.: 09/116,789

[22] Filed: Jul. 16, 1998

[51] Int. Cl.$^7$ ...................................................... A61N 5/00
[52] U.S. Cl. .......................... 607/88; 607/90; 248/118.1; 248/918; 400/715; 235/145 R; 219/217; 219/529
[58] Field of Search ................................ 607/88, 89, 90, 607/108, 111; 248/118, 118.1, 346.01, 560, 633, 918; 400/715; 235/145 R; 345/168; 219/200, 201, 213, 217, 528, 529

[56] References Cited

U.S. PATENT DOCUMENTS

| | | | |
|---|---|---|---|
| 5,416,498 | 5/1995 | Grant | 345/168 |
| 5,439,304 | 8/1995 | Phillips et al. | 400/492 |
| 5,445,349 | 8/1995 | Hart | 248/118 |
| 5,564,844 | 10/1996 | Patterson, Jr. et al. | 400/492 |
| 5,613,786 | 3/1997 | Howell et al. | 400/489 |
| 5,616,140 | 4/1997 | Prescott | 606/10 |
| 5,686,005 | 11/1997 | Wright, Sr. | 607/111 |

OTHER PUBLICATIONS

Newsletter—Alternatives for the Health Conscious Individual, Aug. 1995 (pp. 9–16).
Pamphlet—Medical Electronics—Therapie Mit Energie (Book referencing the products) Undated.

*Primary Examiner*—Linda C. M. Dvorak
*Assistant Examiner*—Bryan K. Yarnell
*Attorney, Agent, or Firm*—Dunlap, Codding & Rogers

[57] ABSTRACT

A therapeutic device for the inhibition of inflammatory diseases in biological tissue and a body part of user. The therapeutic device includes a body member having a work surface and a leading edge. A leading edge is positioned adjacent to the user so that the user extends at least a portion of the body part across the leading edge when working at repetitive motion task on the work surface. The therapeutic device further includes a plurality of lights for generating at least one beam of light positionable on the body part of the user when the user extends the body part across the leading edge. The light beam has a wave length and an intensity sufficient to inhibit the inflammation of the biological tissue in the body part of the user on which the beam of light is positioned.

9 Claims, 2 Drawing Sheets

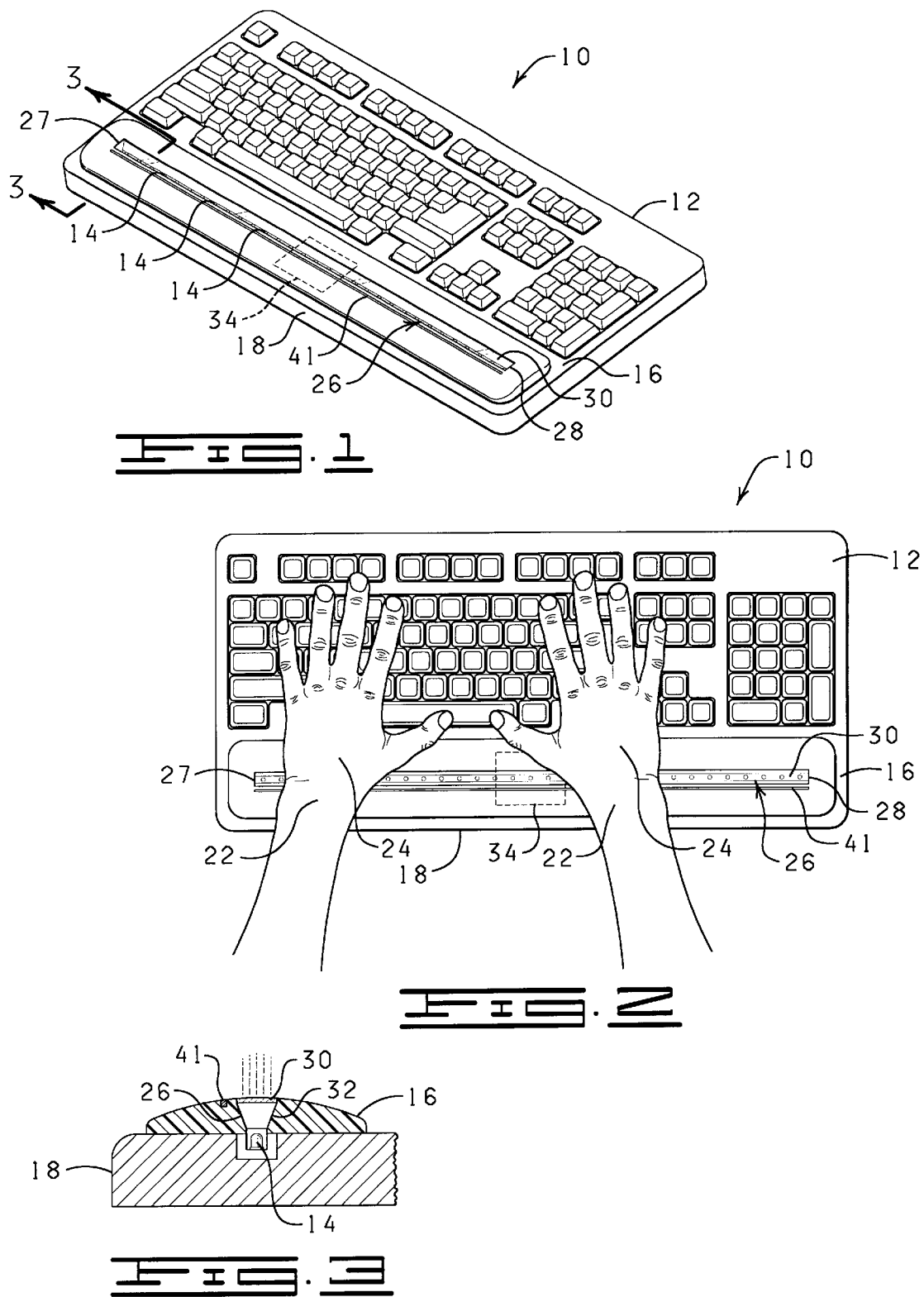

THERAPEUTIC DEVICE

CROSS REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

Carpal tunnel syndrome is a condition involving the inflammation of the median nerve in a wrist. As is well known in the art, carpal tunnel syndrome is typically caused by repetitive motion injury which causes the tendons and nerves that pass through the bony tunnel of the wrist to become inflamed.

Carpal tunnel syndrome is an insidious disease which causes symptoms such as pain, numbness, tingling or a complete loss of feeling in the fingers, hand and arm. These symptoms can be disabling for infected individuals.

Not only is carpal tunnel syndrome an insidious disease for individuals, but it is also very expensive for employers. For example, General Motors claims to have spent over $200,000,000 on carpal tunnel syndrome related injuries in 1993 alone. General Motors also claims that carpal tunnel has thereby become one of General Motors most expensive employee health problems.

Although employers, such as General Motors, have spent great sums of money on the treatment of carpal tunnel syndrome, the current methods for treating carpal tunnel syndrome have generally been unsuccessful.

One current method for treating carpal tunnel syndrome has been to inject steroids into the injured area in an attempt to inhibit the inflammation of the nerves. If this fails, then surgery has been performed to open the tunnel. The surgery for carpal tunnel syndrome involves either the cutting or scraping of the tendons in the wrist. Neither of these methods have exhibited a great deal of success in treating carpal tunnel syndrome.

Recently, a method for treating carpal tunnel syndrome involving the use of low reactive-level laser therapy has been utilized with some success. In this type of therapy, low reactive-level lasers are directed at the individual's wrist to help alleviate the symptoms caused by carpal tunnel syndrome. These lasers have been provided in bandages which are wearable by infected individuals to treat carpal tunnel syndrome.

However, there is a need for a device which inhibits the inflammation of the nerve while uninfected or infected individuals are working to help prevent the occurrence of carpal tunnel syndrome. It is to such a device for inhibiting the inflammation of nerves that the present invention is directed.

BRIEF SUMMARY OF THE INVENTION

Broadly, the present invention is a therapeutic device for the inhibition of inflammation in the nerves in a wrist of a user when the user is working at a repetitive motion task to help prevent carpal tunnel syndrome, for example. The therapeutic device includes a body member having a work surface adapted to permit the user to work at the repetitive motion task thereon, and a leading edge. The leading edge of the body member is positioned adjacent to the user so that the user must extend his wrist across the leading edge when the user is working at the repetitive motion task on the work surface.

The therapeutic device also includes a plurality of lights positioned proximate to the leading edge of the body member. The lights generate at least one beam of light selectively positionable on the wrist of the user when the user extends his wrist across the leading edge to work at the repetitive motion task. The light beams have a wave length and an intensity sufficient to inhibit the inflammation of the nerves in the wrist of the user when the user is working at the repetitive motion task.

In one embodiment of the present invention, the body member is a keyboard. The keyboard includes a leading edge positioned adjacent to the user, and a plurality of keys disposed on a work surface thereof. A plurality of lights are positioned proximate to the leading edge of the keyboard for generating at least one beam of light positionable on the wrist of the user when the user extends his wrist across the leading edge when working at a repetitive motion task, such as typing, for example. The light beams have a wave length and an intensity sufficient to inhibit the inflammation of the nerves in the wrist of the user while the user is typing.

In yet another embodiment of the present invention, the plurality of lights may be pulsed, between an activated state and a deactivated state to provide intermittent light exposure on the wrist of the user.

Thus, it will be appreciated by those skilled in the art that the present invention may be provided as a complete assembled unit which does not have to be worn by the user and which can be predisposed and readably useable by the user at the location where the user is to work on the repetitive motion task.

BRIEF DESCRIPTION OF THE SEVERAL VIEWS OF THE DRAWING

FIG. 1 is a perspective view of a therapeutic device constructed in accordance with the present invention.

FIG. 2 is a plan view of the therapeutic device depicted in FIG. 1 illustrating a user's hands and wrists being positioned over the therapeutic device.

FIG. 3 is a partial, cross-sectional view of the therapeutic device taken along the lines 3—3 in FIG. 1.

DETAILED DESCRIPTION OF THE INVENTION

Figure 4:
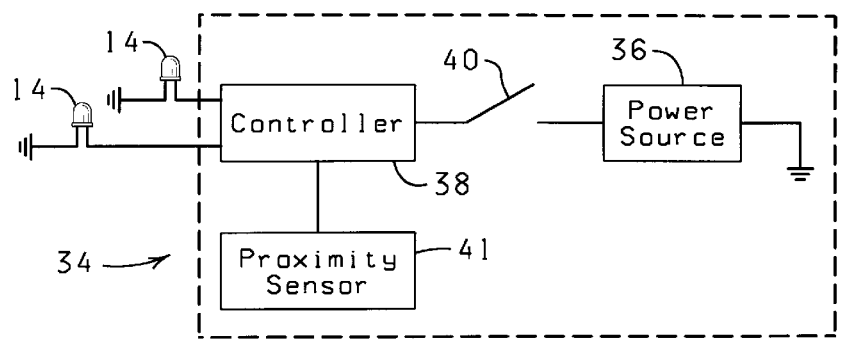
FIG. 4 is a schematic diagram illustrating a control circuit constructed in accordance with the present invention.

Referring now to the drawings and more particularly to FIGS. 1 and 2, shown therein and designated by the general reference numeral 10 is a therapeutic device for the inhibition of inflammatory diseases, such as carpal tunnel syndrome caused by a repetitive motion task, such as typing. The therapeutic device 10 includes a body member 12 and a plurality of lights 14 (only three of the lights have been labeled for purposes of clarity).

The body member 12 has a work surface 16 and a leading edge 18. The leading edge 18 is positioned adjacent to the user so that the user must extend his wrist 22 and hands 24 (as shown in FIG. 2) across the leading edge 18 when the user is working on the work surface 16. As shown in FIGS. 1 and 2, in one embodiment the body member 12 can be a keyboard. However, it should be understood that the body member 12 can be in the form of other equipment.

The body member 12 is provided with an elongated slot 26 formed in the body member 12, near the leading edge 18. The plurality of lights 14 are contiguously disposed in the elongated slot 26 so that the beams of light being generated by the lights 14 are directed out of the elongated slot and are thereby positionable on the wrists 22 and hands 24 of the user when the user extends his wrists 22 and hands 24 across the leading edge 18 when typing, for example.

The lights 14 are adapted to produce light beams having a wave length and an intensity sufficient to inhibit the inflammation of the nerves in the wrist 22 of the user. In one embodiment, the lights 14 produce light having a wave length encompassed by the color red. The light produced by the lights 14 can have a wavelength in a range between about 600 to about 830 nanometers. For example, the lights 14 can be a model S1040CR3K-120BAC obtainable from LEDTRONICS, INC., 4009 Pacific Coast Highway, Torrance, Calif.

Shown in FIG. 3 is a cross-sectional view of the body member 12 taken along the lines 3—3 depicted in FIG. 1. The elongated slot 26 has a first end 27 and a second end 28. The plurality of lights 14 are contiguously disposed in the elongated slot 26 from the first end 27 to the second end 28 thereof.

To direct the light beams generated by the lights 14 away from the eyes of the user, a lens 30 is provided in the elongated slot 26 generally above the lights 14, substantially as shown in FIG. 3. The elongated slot 26 is provided with an upper tapered portion 32 which is best shown in FIG. 3 to direct the light being created from the plurality of lights 14 through the lens 30. The upper tapered portion 32 extends from the first end 27 of the elongated slot 26 to the second end 28 thereof.

Shown in FIG. 4 is a control circuit 34 for controlling the operation of the lights 14. The control circuit 34 includes a power source 36, a controller 38 and a manual switch 40. The manual switch 40 is disposed generally in between the power source 36 and the controller 38 and functions as a manual override to permit the user to selectively activate and deactivate the controller 38, and thereby the lights 14. When the therapeutic device 10 is in the form of a keyboard, the manual switch 40 can be the switch which activates the computer to which the keyboard is connected. The controller 38 can also be provided with a proximity sensor 41, for a purpose to be describe hereinafter.

When activated, the controller 38 selectively controls the lights 14 in at least three modes of operation. In the first mode, the lights 14 are activated continuously. In the second mode, the lights 14 are selectively activated and deactivated in an intermittent pattern. In a third mode, the proximity sensor 41 senses the presence of a body part, such as the wrists 22 and/or hands 24, of the user being disposed in close proximity to the elongated slot 26 formed in the body member 12. The proximity sensor 41 then outputs a signal of such detection to the controller 38. Upon detecting the signal from the proximity sensor 41, the controller 38 is adapted to selectively activate and deactivate the lights 14. In one embodiment, the controller 38 is adapted to selectively activate the particular lights 14 disposed generally underneath the wrist 22 of the user, and to deactivate the lights 14 which are not disposed generally underneath the wrist 22 of the user. The advantage of activating only the lights 14 which are underneath the wrist 22 of the user is to conserve energy and to inhibit the amount of light which is radiated past the wrist 22.

In use, the user first actuates the manual switch 40 to provide electricity from the power source 36 to the controller 38. In response thereto, the controller 38 outputs signals to the lights 14 as previously discussed. Once the controller 38 has been activated, the user extends the hand 24 and wrist 22 of the user across the leading edge 18 of the body member 12 to begin working at the repetitive motion task on the work surface 16 of the body member 12. While the user is working at the repetitive motion task on the work surface 16, the lights 14 generate light beams positioned on the wrist 22 and/or hands 24 of the user to inhibit the amount of inflammation in the wrist 22 and hands 24. This inhibition in the inflammation of the wrist 22 and hands 24 while the user is working at the repetitive motion task is believed to inhibit the occurrence of inflammation in the wrist 22 and hands 24 and to thereby help prevent the occurrence of inflammatory diseases, such as carpal tunnel syndrome.

Figure 5:
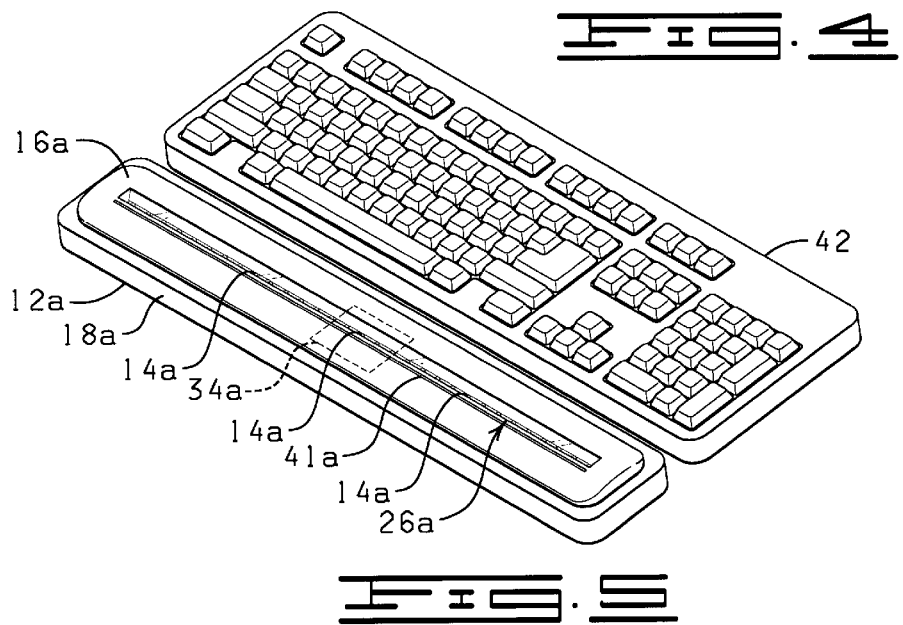
FIG. 5 is a perspective view of a second embodiment of a therapeutic device constructed in accordance with the present invention.
Figure 6:
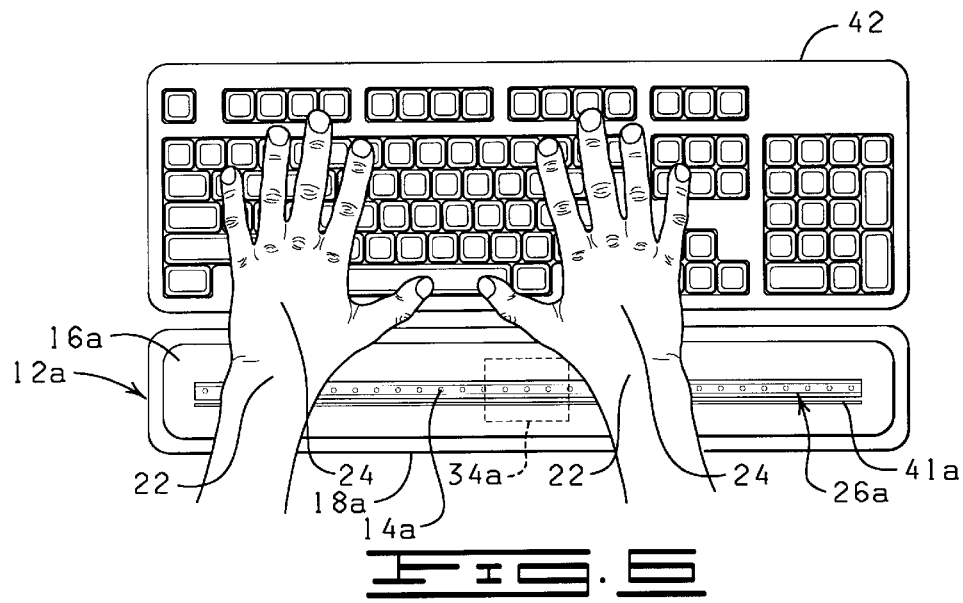
FIG. 6 is a plan view of the therapeutic device depicted in FIG. 5 illustrating a user's hands and wrists being positioned over the therapeutic device.

Embodiments of FIGS. 5 and 6

Referring now to FIGS. 5 and 6, shown therein and designated by the general reference numeral 10a is another embodiment of a therapeutic device constructed in accordance with the present invention. The therapeutic device 10a is provided with a body member 12a and a plurality of lights 14a. Only three of the lights are designated by the reference numeral 14a for purposes of clarity.

The body member 12a is provided with a work surface 16a and a leading edge 18a. The leading edge 18a is positioned adjacent to the user such that the user extends the user's wrist 22 and hands 24 past the leading edge 18a when the user is utilizing the work surface 16a, to provide support for the user's wrists 22 when the user is working at a repetitive motion task, such as typing. In this particular embodiment, the body member 12a is in the form of a wrist rest provided adjacent to a keyboard 42.

The body member 12a is provided with an elongated slot 26a which is identical in construction and function as the elongated slot 26, hereinbefore described as reference FIGS. 1–3. The lights 14a are contiguously disposed in the elongated slot 26 in an identical manner as the lights 14 are disposed in the elongated 26 as hereinbefore described with reference to FIGS. 1–3. The lights 14a are selectively activated and deactivated by a control circuit 34a which is identical in construction and function as the control circuit 34, hereinbefore described with reference to FIG. 4. The control circuit 34a includes a proximity sensor 41a which is identical in construction and function as the proximity sensor 41, hereinbefore described with reference to FIG. 4.

Because inflammatory diseases in body parts of users caused by repetitive motion injury is not only a disabling disease for individuals, but is also very expensive to our employers, a need for the therapeutic devices which have been shown and described herein has been recognized in the art. One important advantage of the present invention is that the lights 14 and 14a, and the body members 12 and 12a may be provided as a complete assembled unit. Thus, the therapeutic devices 10 and 10a of the present invention do not have to be worn by the user, and can be predisposed and readily useable by the user at the location where the user is to work on the repetitive motion task.

Changes may be made in the embodiments of the invention described herein, or in the parts or the elements of the embodiments described herein or in the steps or sequence of steps of the methods described herein. Without departing from the spirit and/or the scope of the invention as defined in the following claims.

What is claimed is:

1. A therapeutic device for inhibiting an inflammatory response in a body part of a user, comprising:

a body member having a work surface and a leading edge, the leading edge positionable adjacent to the user so that the user extends at least a portion of the body part across the leading edge when working at a repetitive motion task on the work surface; and a plurality of lights positioned on the body member for generating at least one beam of light positionable on the body part of the user when the user extends the body part across the leading edge, the beam of light having a wave length and an intensity sufficient to inhibit an inflammatory response in the body part of the user on which the beam of light is positionable.

2. A therapeutic device, as recited in claim 1 wherein the body member is a keyboard.

3. A therapeutic device as defined in claim 1, wherein the body member is provided with an elongated slot extending near the leading edge thereof, and wherein the lights are positioned within the elongated slot.

4. A therapeutic device as defined in claim 3, further comprising a lens disposed in the elongated slot and positioned such that the beam of light generated by the lights passes through the lens before contacting the body parts of the user.

5. A therapeutic device for the inhibiting of an inflammatory response in the nerves in a wrist of a user when the user is typing, the therapeutic device comprising:

a keyboard having a leading edge and a plurality of keys disposed on a work surface thereof, the leading edge being positionable adjacent to the user so that the user can extend at least a portion of his wrist across the leading edge when typing; and light means positioned on the keyboard for generating at least one beam of light selectively positionable on the wrist of the user when the user extends his wrist across the leading edge, the beam of light having a wave length and intensity sufficient to inhibit an inflammatory response in the nerves in the wrist of the user on which the beam of light is positionable.

6. A therapeutic device as defined in claim 5, wherein the wave length of the beam of light produced by the light means is in a range between about 600 nanometers to about 830 nanometers.

7. A therapeutic device as defined in claim 6, wherein the keyboard is provided within an elongated slot extending near the leading edge thereof, and wherein the light means are positioned within the elongated slot.

8. A therapeutic device for the inhibiting of an inflammatory response in a wrist of a user when the user is working at a repetitive motion task, the therapeutic device comprising:

a wrist rest having a work surface and a leading edge, the leading edge being positionable adjacent to the user such that the user extends the user's wrist and hands past the leading edge when the user is working at the repetitive motion task, and the work surface being adapted to provide support for the user's wrist when the user is working at the repetitive motion task; and light means positioned on the wrist rest for generating at least one beam of light selectively positionable on the wrist of the user when the user extends at least one wrist across the leading edge, the beam of light having a wave length and an intensity sufficient to inhibit an inflammatory response in at least one wrist of the user.

9. A therapeutic device as defined in claim 8, wherein the wave length of the beam of light produced by the light means is in a range between about 600 nanometers to about 830 nanometers.

* * * * *